(12) United States Patent
Jeong et al.

(10) Patent No.: US 11,060,997 B2
(45) Date of Patent: Jul. 13, 2021

(54) QUANTUM DOT BIOSENSOR

(71) Applicants: LG Chem, Ltd., Seoul (KR); Korea University Research and Business Foundation, Seoul (KR)

(72) Inventors: Kwang Seob Jeong, Seoul (KR); Hang Beum Shin, Daejeon (KR); Young Do Jeong, Daejeon (KR); Bit Na Yoon, Seoul (KR); Dong Sun Choi, Gyeonggi-do (KR); Ju Yeon Jeong, Gyeonggi-do (KR)

(73) Assignees: LG Chem, Ltd.; Korea University Research and Business Foundation

( * ) Notice: Subject to any disclaimer, the term of this patent is extended or adjusted under 35 U.S.C. 154(b) by 0 days.

(21) Appl. No.: 16/346,720

(22) PCT Filed: Nov. 2, 2017

(86) PCT No.: PCT/KR2017/012332
§ 371 (c)(1),
(2) Date: May 1, 2019

(87) PCT Pub. No.: WO2018/084601
PCT Pub. Date: May 11, 2018

(65) Prior Publication Data
US 2020/0072787 A1 Mar. 5, 2020

(30) Foreign Application Priority Data

Nov. 2, 2016 (KR) .................. 10-2016-0144849
Nov. 2, 2017 (KR) .................. 10-2017-0145154

(51) Int. Cl.
*G01N 27/414* (2006.01)
*G01N 33/543* (2006.01)
(Continued)

(52) U.S. Cl.
CPC ..... *G01N 27/4145* (2013.01); *G01N 27/4146* (2013.01); *G01N 27/4148* (2013.01);
(Continued)

(58) Field of Classification Search
CPC .......... H01L 29/0665; H01L 29/78696; G01N 27/4145; G01N 27/4146; G01N 27/4148; G01N 33/54373
See application file for complete search history.

(56) References Cited

U.S. PATENT DOCUMENTS

2009/0008629 A1* 1/2009 Matsumoto ......... H01L 21/0217
257/24
2010/0019226 A1* 1/2010 Kahya .................... B82Y 10/00
257/24
(Continued)

FOREIGN PATENT DOCUMENTS

CN 101923065 A 12/2010
CN 102738191 A 10/2012
(Continued)

OTHER PUBLICATIONS

Extended European Search Report including the Written Opinion for Application No. 17867342.2 dated Sep. 18, 2019, 9 pages.
(Continued)

*Primary Examiner* — Matthew E Warren
(74) *Attorney, Agent, or Firm* — Lerner, David, Littenberg, Krumholz & Mentlik, LLP

(57) ABSTRACT

A biosensor comprising a substrate, a gate electrode provided on the substrate, an insulating layer provided on the gate electrode, a source electrode and a drain electrode, provided on the insulating layer, respectively, an n-type channel provided between the source electrode and the drain electrode, and a quantum dot layer provided on the n-type channel and provided so as to have electronic transition
(Continued)

energy capable of resonating with vibration energy of a target biological material.

17 Claims, 3 Drawing Sheets

(51) Int. Cl.
*H01L 29/06* (2006.01)
*H01L 29/786* (2006.01)

(52) U.S. Cl.
CPC ... *G01N 33/54373* (2013.01); *H01L 29/0665* (2013.01); *H01L 29/78696* (2013.01)

(56) References Cited

U.S. PATENT DOCUMENTS

| | | | | |
|---|---|---|---|---|
| 2015/0097193 | A1* | 4/2015 | Yap | H01L 49/006 257/76 |
| 2018/0120254 | A1* | 5/2018 | Jain | G01N 33/5438 |
| 2018/0313784 | A1* | 11/2018 | White | H01L 29/127 |

FOREIGN PATENT DOCUMENTS

| | | | |
|---|---|---|---|
| CN | 105552131 | A | 5/2016 |
| EP | 3163296 | A1 | 5/2017 |
| JP | 2007529747 | A | 10/2007 |
| JP | 2009229341 | A | 10/2009 |
| JP | 201392479 | A | 5/2013 |
| KR | 20140044538 | A | 4/2014 |
| KR | 20140077745 | A | 6/2014 |
| KR | 20150072888 | A | 6/2015 |
| KR | 101616560 | B1 | 4/2016 |
| WO | 2016042210 | A1 | 3/2016 |

OTHER PUBLICATIONS

International Search Report dated Feb. 6, 2018, in PCT/KR2017/012332, 2 pages.

Chinese Search Report for Application No. 2017800680789, dated Nov. 9, 2020, 2 pages.

Anchala, Purohit SP, Mathur KC. Third harmonic generation in intraband transitions of spherical silicon quantum dots. Journal of Applied Physics. Nov. 1, 2012;112(9):094306.

Guyot-Sionnest P, Hines MA. Intraband transitions in semiconductor nanocrystals. Applied Physics Letters. Feb. 3, 1998;72(6):686-8.

Lhuillier E, Scaratagio M, Hease P, Nadal B, Aubin H, Xu XZ, Lequeux N, Patriarche G, Ithurria S, Dubertret B. Infrared photodetection based on colloidal quantum-dot films with high mobility and optical absorption up to THz. Nano letters. Feb. 10, 2016;16(2)1282-6.

Novoselov KS, Geim AK, Morozov SV, Jiang D, Zhang Y, Dubonos SV, Grigorieva IV, Firsov AA. Electric field effect in atomically thin carbon films. science. Oct. 22, 2004;306(5696):666-9.

'Quantum Dot, Wikipedia article retrieved from internet—https://web. archive. org/web/20150326020921/https://en. wikipedia. org/wiki/Quantum_dot, Dec. 14, 2017 at 10:27; 20 pages.

* cited by examiner

[Figure 1]
10
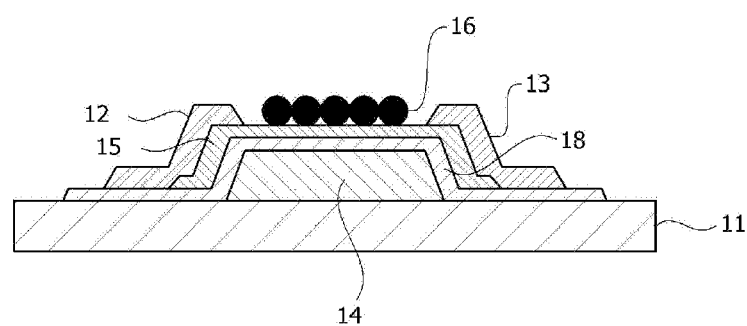
[Figure 2]
100
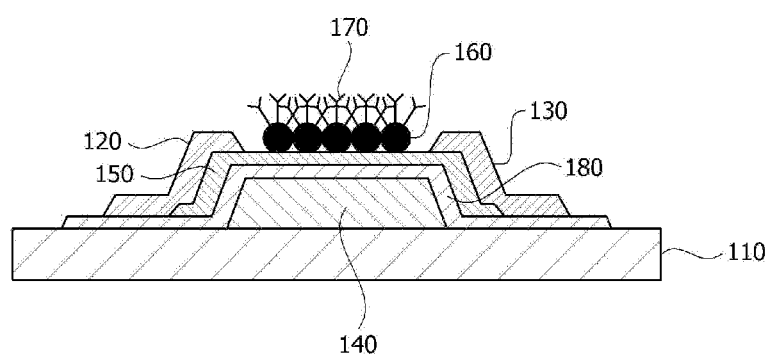

[Figure 3]
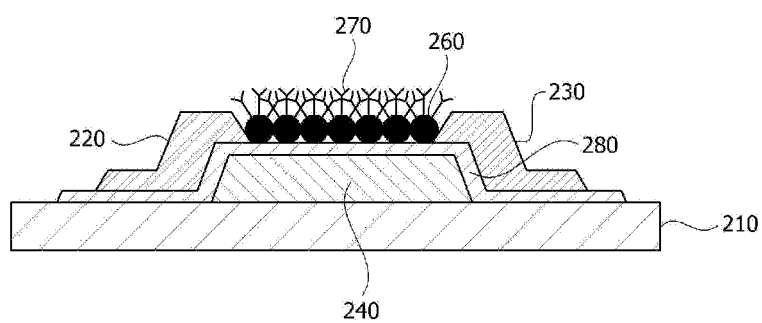
[Figure 4]
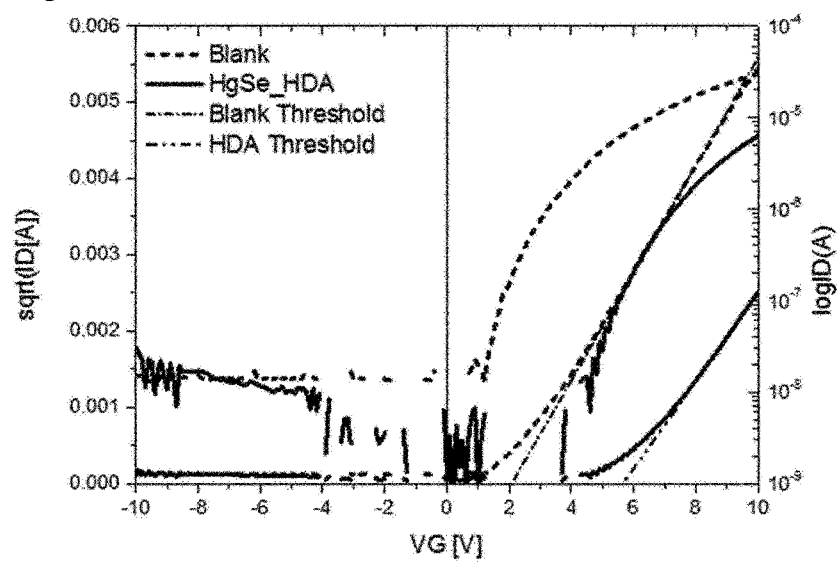

[Figure 5]
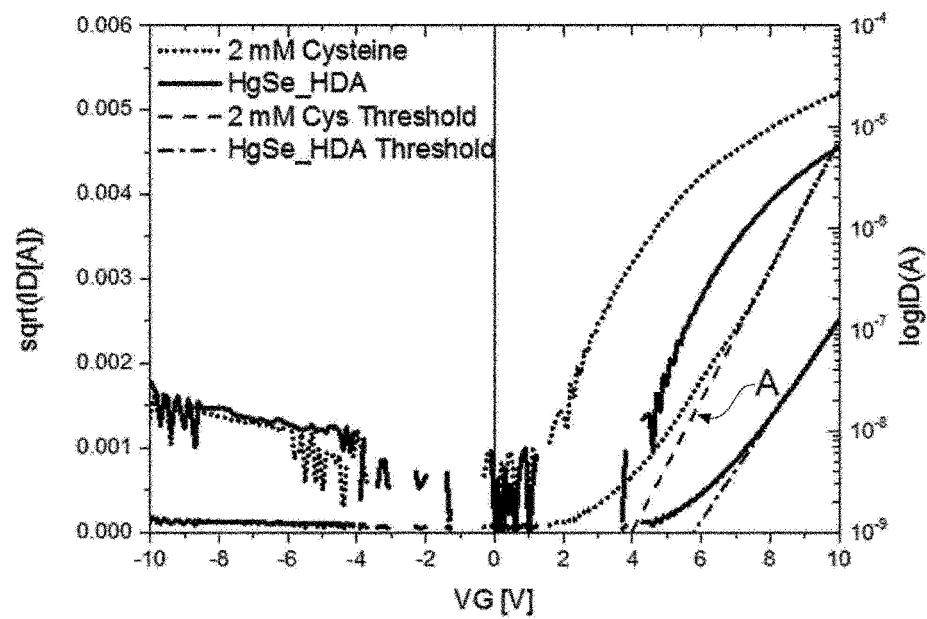

QUANTUM DOT BIOSENSOR

CROSS-REFERENCE TO RELATED APPLICATIONS

The present application is a national phase entry under 35 U.S.C. § 371 of International Application No. PCT/KR2017/012332 filed Nov. 2, 2017, which claims priority from Korean Patent Application No. 10-2016-0144849 filed on Nov. 2, 2016, and Korean Patent Application No. 10-2017-0145154 filed on Nov. 2, 2017, all of which are incorporated herein by reference.

TECHNICAL FIELD

The present invention relates to a biosensor, and particularly, relates to a biosensor using quantum dots.

BACKGROUND ART

As quantum dots control their size, they can easily control energy bandgaps, thereby being used as a light emitting material by using such characteristics. In addition, the quantum dots can generate electric charges by absorbing light of various wavelengths, and thus can be utilized as a material for a biosensor and a light detecting sensor in addition to the light emitting material.

On the other hand, research and development, and investment for monitoring metabolites, such as immunoglobulin E, which are small biomolecules, or specific biological materials such as glucose, modified genes, cancer cells or environmental hormones in real time are being actively conducted.

There are electrochemical biosensors, piezoelectric biosensors, optical biosensors or thermal biosensors, and the like as technical methods of commonly used biosensors, and in many cases, they may change equilibrium to a real-time sample concentration by destroying the sample during measurement. In addition, because of detection through additional biological markers, additional procedures for adding biological marker materials are required, which have a disadvantage in that the density of the grafted biological marker is low.

DISCLOSURE

Technical Problem

It is a problem to be solved by the present invention to provide a biosensor capable of inducing a fine potential difference to a current change and measuring it, wherein the potential difference is generated when the potential of a quantum dot layer is changed according to electronic-vibrational energy transfer between the quantum dot layer and target biomolecules.

In addition, it is another problem to be solved by the present invention to provide a biosensor capable of effectively transferring electric charges of a collecting part to a sensing part.

Technical Solution

To solve the above-described problems, according to one aspect of the present invention, there is provided a biosensor comprising a substrate, a gate electrode provided on the substrate, an insulating layer provided on the gate electrode, a source electrode and a drain electrode, provided on the insulating layer, respectively, an n-type channel provided between the source electrode and the drain electrode, and a quantum dot layer provided on the n-type channel and provided so as to have electronic transition energy capable of resonating with vibration energy of a target biological material.

Also, the quantum dots constituting the quantum dot layer may be colloidal quantum dots.

Furthermore, the biosensor may further comprise a collecting part for collecting a biological material to be analyzed, and the collecting part may be provided on or included in the quantum dot layer.

In addition, according to another aspect of the present invention, there is provided a biosensor comprising a substrate, a gate electrode provided on the substrate, an insulating layer provided on the gate electrode, a source electrode and a drain electrode, provided on the insulating layer, respectively, and a quantum dot layer provided so as to electrically connect the source electrode and the drain electrode and provided so as to have electronic transition energy capable of resonating with vibration energy of a target biological material. Also, the quantum dots constituting the quantum dot layer may be colloidal quantum dots. Furthermore, the biosensor may further comprise a collecting part for collecting a biological material to be analyzed, and the collecting part may be provided on or included in the quantum dot layer.

Advantageous Effects

As described above, according to the biosensor related to at least one example of the present invention, it can measure the current change of the quantum dot layer depending on the electronic-vibrational energy transfer between the quantum dot layer and the target biomolecules, thereby detecting the biological material. In addition, the electric charges of the collecting part can be effectively transferred to the sensing part, and the efficiency of the biosensor can be improved.

BRIEF DESCRIPTION OF DRAWINGS

FIG. 1 is a schematic sectional view showing a biosensor according to a first example of the present invention.

FIG. 2 is a schematic sectional view showing a biosensor according to a second example of the present invention.

FIG. 3 is a schematic sectional view showing a biosensor according to a third example of the present invention.

FIGS. 4 and 5 are graphs showing detection results of cysteine.

DETAILED DESCRIPTION

Hereinafter, a biosensor according to one example of the present invention will be described in detail with reference to the accompanying drawings.

In addition, the same or similar reference numerals are given to the same or corresponding components regardless of reference numerals, of which redundant explanations will be omitted, and for convenience of explanation, the size and shape of each constituent member as shown may be exaggerated or reduced.

FIG. 1 is a schematic sectional view showing a biosensor (10) according to a first example of the present invention.

The present invention provides a biosensor (100) comprising a quantum dot layer formed on an n-type channel. In addition, the quantum dot layer is provided so as to have electronic transition energy capable of resonating with vibration energy of a target biological material.

Referring to FIG. 1, the biosensor (10) related to the first example comprises a substrate (11), a gate electrode (14), an insulating layer (18), a source electrode (12), a drain electrode (13), an n-type channel (15), and a quantum dot layer (16).

Specifically, the biosensor (10) related to one example of the present invention comprises a substrate (11), a gate electrode (14) provided on the substrate (11), an insulating layer (18) provided on the gate electrode (14), and a source electrode (12) and a drain electrode (13), provided on the insulating layer (18), respectively. Also, the biosensor (10) comprises an n-type channel (15) provided between the source electrode (12) and the drain electrode (13), and a quantum dot layer (16) provided so that the current flows and provided on the n-type channel (15).

Also, the n-type channel (15) is provided to electrically connect the source electrode (12) and the drain electrode (13).

Furthermore, the quantum dot layer (16) is provided so as to have the electronic transition energy (in-band electronic transition energy) capable of resonating with the vibration energy of the target biological material.

In addition, the quantum dot layer (16) may also be provided to electrically connect the source electrode (12) and the drain electrode (13) and the quantum dot layer (16) may also be provided so as not to electrically connect the source electrode (12) and the drain electrode (13).

The quantum dot layer (16) is one arranged such that a number of quantum dots having a spherical shape form a layer, where the quantum dots can easily control an energy gap of an electron structure by controlling the size and composition thereof.

The operation principle of the biosensor (10) using the quantum dots is to detect the current flowing in the quantum dot layer in real time and to use the current change of the quantum dot layer (16). For example, in the case of the biosensor (10) using the quantum dots, it is combined with a field-effect thin film transistor (TFT), which can be utilized.

Particularly, it can induce a fine potential difference to a current change and measure it, wherein the potential difference is generated when the potential of a quantum dot layer (16) is changed according to electronic-vibrational energy transfer between the quantum dot layer (16) and a target biological material.

Also, the quantum dot layer (16) may be formed in a film form.

In the field-effect thin film transistor, the change of the functional group occurring on the surface of the quantum dot layer (16) changes the potential of the quantum dots, where electrons convert this fine potential change into the current change of a conduction channel of the n-type channel to amplify it. In summary, the change of the surface potential at the quantum dots indicates the current change in the thin film transistor soon and also appears as a change in threshold voltage, which can be measured and applied as the biosensor.

Specifically, when a voltage equal to or higher than the threshold voltage is applied between the source electrode and the gate electrode in the thin film transistor (TFT), a conduction channel is formed in the n-type channel, through which electrons can move between the source electrode (12) and the drain electrode (13). And, the potential of the quantum dots may also affect the n-type conduction channel, thereby affecting the threshold voltage.

Therefore, the biosensor (10) according to the present invention can observe the potential difference induced in the quantum dot layer (16) when the current is measured in real time between the source electrode (12) and the gate electrode (14), which is provided so as to measure the current changed according to the specific electronic-vibrational energy transfer transferred from the target biomolecules to the quantum dot layer (16). In addition, the current to be measured causes the current change, as the in-band transition energy of the quantum dots is absorbed by vibration of the specific functional group of the target biomolecule.

Also, the increase of the potential by the vibration of the target biomolecule is a new and highly feasible measurement method, where the potential value is proportional to the concentration of the biomolecules.

Furthermore, since the energy transfer is by coupling between the quantum dot layer (16) and the biomolecule vibration, information on the physical distance between the biomolecule and the quantum dot layer (16) can also be measured.

Besides, the usable n-type channel (15) in the present invention may include any one of n-type materials selected from the group consisting of IGZO, ZnO, ZTO, IZO, IHZO, AlN, InN, GaN and InGaN.

In particular, the n-type channel (15) including IGZO is preferred, because it has excellent optical transparency, amorphous structure and high electron mobility, and quantum dots can also be directly functionalized on the IGZO channel. Furthermore, the IGZO channel can directly function as an active matrix backplane, which has an advantage that a separate integration process can be omitted.

Also, it is preferred that as the usable quantum dots in the present invention, colloidal quantum dots are used. When the colloidal quantum dots are used, they can be formed by a simple method such as spin coating on the n-type channel (15), and the quantum dots can be uniformly distributed.

As the quantum dots, any one or more selected from the group consisting of CdS, CdSe, CdTe, ZnS, ZnSe, ZnTe, ZnO, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, CdHgZnTe, CdZnSeS, CdZnSeTe, CdZnSTe, CdHgSeS, CdHgSeTe, CdHgSTe, HgZnSeS, HgZnSeTe, HgZnSTe; GaN, GaP, GaAs, GaSb, InN, InP, InAs, InSb, GaNP, GaNAs, GaNSb, GaPAs, GaPSb, InNP, InNAs, InNSb, InPAs, InPSb, GaInNP, GaInNAs, GaInNSb, GaInPAs, GaInPSb, SnS, SnSe, SnTe, PbS, PbSe, PbTe, SnSeS, SnSeTe, SnSTe, PbSeS, PbSeTe, PbSTe, SnPbS, SnPbSe, SnPbTe, SnPbSSe, SnPbSeTe, SnPbSTe, Si, Ge, SiC and SiGe can be used.

Particularly, the biosensor (10) related to one example of the present invention can use the quantum dot layer (16) having electronic transition in the infrared region, especially the mid-infrared region. In this case, quantum dots capable of absorbing light in the infrared region, particularly a wavelength of 1000 nm to 20 μm, and preferably a wavelength of 1000 nm to 8000 nm, can be used by adjusting the type or size of the quantum dots. Also, since the colloidal quantum dots can be processed in a large area at low cost, it is preferred to use the colloidal quantum dots in the present invention.

In addition, as the quantum dots, ligand-substituted quantum dots can be used. The quantum dots may be substituted with at least one ligand of an organic ligand and an inorganic ligand. An example of a ligand, which is a quantum dot, may include EDT (ethanedithol), BDT (butanethiol), MPA (mercaptocarboxylic acid), CTAB (Cetyltrimethylammonium bromide), HTAC (hexadecyltrimethylammonium chloride), TBAI (tetrabutylammonium iodide) or Na2S.

The quantum dots have a structure surrounded by an oleic acid ligand for dispersion and stability of the colloidal solution. The quantum dots in this state can also be applied to the biosensor, but since the oleic acid ligand has a long chain structure, electrons generated in the quantum dots are disturbed to move to the n-type channel (15). Therefore, it is preferred to substitute the ligand with a ligand having a shorter chain structure. When the ligand-substituted quantum dots are used, for example, a method may be used, in which the ligand is substituted by forming the quantum dots surrounded by the oleic acid ligand on the n-type channel (15) and then reacting them with the ligand.

Alternatively, the organic material ligand of the colloidal quantum dot layer may be substituted with a monomolecular organic ligand or inorganic ligand to improve accessibility of the target biomolecule and to facilitate resonance of the vibration mode of the functional group in the biomolecule and the in-band transition of the quantum dot layer.

In one example, a bidentate ligand such as EDT, BDT or MPA as described above will be used as the organic ligand for electric charge transfer, which may be mixed with an inorganic ligand to form the film structure of the colloidal quantum dot layer uniformly.

After synthesizing them using a compound providing halogen ions such as CTAB (Cetyltrimethylammonium bromide), CTACl (Cetyltrimethylammonium chloride) and TBAI (Tributylammonium iodide), the used oranic ligands may be substituted with halogen ions such as $Br^-$, $Cl^-$ or $I^-$. The substitution process can be performed at room temperature by allowing the halogen ions to exist on the film composed of the colloidal quantum dot layer surrounded by the organic ligands for a few minutes. The thickness of the film can be increased sequentially, and the thickness can be from 10 nm to 300 nm. Because the halogen is an atomic ligand, it has no vibration motion by the ligand, so that it may remove a molecule to cause resonance phenomenon with the target biomolecule in the mid-infrared region. Accordingly, it is possible to obtain more improved and stable electric signals.

As another method for substituting it with inorganic ligands, a method using a polarity difference between a polar solution and a non-polar solution may be used. When the colloidal quantum dot solution modified with non-polar organic ligands is stirred with the polar inorganic ligand solution at room temperature, the polar ligands are modified on the surface of the colloidal quantum dots and the dielectric constant of the colloidal quantum dots is increased. Thus, colloidal quantum dots modified with the inorganic ligands are present in the polar solution. The colloidal quantum dot solution modified with the polar inorganic ligands has an advantage that the colloidal solution can be coated on the surface.

Also, the insulating layer (18) may be formed of $SiO_2$, $Al_2O_3$, $TiO_2$, $ZrO_2$, $HfO_2$ or $SiN_x$, and the like.

Furthermore, the gate electrode (14) may be formed of a metal, which may be selected, for example, from the group consisting of Cr, Mo, Al, Ti/Au, Ag, Cu, and Pt.

In addition, the source electrode (12) and the drain electrode (13) may be formed of a metal, respectively, which may be selected, for example, from the group consisting of Cr, Ti/Au, Mo, Al, Ag, Cu, Pt and W.

Besides, the remaining structures other than the insulating layer (18), the n-type channel (15), the quantum dot layer (16), and the source and drain electrodes (12, 13), as described above are not particularly limited as long as they can be usually used in the biosensor (10).

For example, as the substrate (11), a glass substrate or a plastic substrate may be used, which is not particularly limited as long as it is applied to the biosensor (10). Also, the arrangement of each component in the biosensor (10) is not particularly limited as long as it is applied to the conventional biosensor (100).

FIG. 2 is a schematic sectional view showing a biosensor (100) according to a second example of the present invention.

Referring to FIG. 2, the biosensor (100) comprises a substrate (110), a gate electrode (140), an insulating layer (180), a source electrode (120), a drain electrode (130), an n-type channel (150), and a quantum dot layer (160) and a collecting part (170). That is, the biosensor (100) according to the second example may further comprise a collecting part (170) for collecting a target biological material, which is provided in the quantum dot layer (160). In the second example, the other components are the same as those of the biosensor (10) described in the first example.

The biosensor (100) related to the second example comprises a substrate (110), a gate electrode (140) provided on the substrate (110), an insulating layer (180) provided on the gate electrode (140), and a source electrode (120) and a drain electrode (130), provided on the insulating layer (180), respectively. Also, the biosensor (100) comprises an n-type channel (150) provided between the source electrode (120) and the drain electrode (130) so as to electrically connect the source electrode (120) and the drain electrode (130). The source electrode (120) and the drain electrode (130) are provided over the insulating layer (180) and the n-type channel (150), respectively. In addition, the biosensor (100) comprises a quantum dot layer (160) provided so that the current flows, provided on the n-type channel (150) and provided so as to have electronic transition energy capable of resonating with vibration energy of a target biological material, and a collecting part (170) for collecting the target biological material, which is provided in the quantum dot layer (160).

The collecting part (170) may comprise a plurality of collection molecules. Also, the plurality of collection molecules may be immobilized on the curved surface portion of the quantum dot layer. That is, the quantum dot layer (160) may be provided to have a curved surface. Furthermore, the quantum dot layer (160) may be produced in a film form.

In the field-effect thin film transistor, the current change of the quantum dot layer causes its electrons to move to the conduction channel of the n-type channel to generate a change in the threshold voltage, which can be measured and applied as the biosensor.

Specifically, when a voltage equal to or higher than the threshold voltage is applied between the source electrode and the gate in the thin film transistor (TFT), a conduction channel is formed in the n-type channel (150), through which electrons can move between the source electrode (120) and the drain electrode (130).

Therefore, after a certain amount of voltage within approximately +/−5 V of the threshold voltage is applied between the source electrode and the gate electrode, the biosensor (100) according to the present invention is provided so as to measure the changed current, by a real-time measurement of the current flowing in the quantum dot layer (160), where a fine potential difference is induced in the quantum dot layer (160) according to a specific electric-vibrational energy transfer between the target biomolecules collected in the collecting part and the quantum dot layer (160) and the current is changed in the n-type channel (150). The current to be measured causes the current change, as the in-band transition energy is absorbed by vibration of the specific functional group of the target biomolecule.

Also, the potential change in the quantum dots by the vibration of the target biomolecule is a new and highly feasible measurement method, where the change of the current values is proportional to the concentration of the biomolecule.

Furthermore, the advantage of the thin film transistor by the quantum dot layer (160) in this manner is that it can characteristically respond to biomolecule changes of a specific energy and amplify the signal.

In addition, since the energy transfer is by coupling between the quantum dot layer (160) and the biomolecule vibration, information on the physical distance between the biomolecule and the quantum dot layer (160) can also be measured.

The insulating layer (180) may also be formed of SiO2, Al2O3, TiO2, ZrO2, HfO2 or SiNx, and the like.

Also, the gate electrode (140) may be formed of a metal, which may be, for example, selected from the group consisting of Cr, Mo, Al, Ti/Au, Ag, Cu and Pt.

Furthermore, the source electrode (120) and the drain electrode (130) may be each formed of a metal, which may be, for example, selected from the group consisting of Cr, Ti/Au, Mo, Al, Ag, Cu, Pt and W.

Besides, the remaining structures other than the insulating layer (180), the n-type channel (150), the quantum dot layer (160), the collecting part (170), and the source and drain electrodes (120, 130), as described above, are not particularly limited as long as they can be usually used in the biosensor (100).

For example, as the substrate (110), a glass substrate or a plastic substrate may be used, which is not particularly limited as long as it is applied to the biosensor (100). Also, the arrangement of each component in the biosensor (100) is not particularly limited as long as it is applied to the conventional biosensor (100).

Also, collection molecules may be immobilized on the quantum dot layer (160). The collection molecules can specifically bind to the target biological material to be analyzed and collect the biological material. The reaction between the collection molecules and the biological material may be, for example, nucleic acid hybridization, an antigen-antibody reaction or an enzyme binding reaction. Furthermore, the biological material may be immobilized on the surface of the collection molecule. For example, the collection molecules may be, for example, proteins, cells, viruses, nucleic acid organic molecules or inorganic molecules. When the collection molecules are proteins, the protein may be, for example, an antigen, an antibody, a substrate protein, an enzyme or a coenzyme. When the collection molecules are nucleic acids, the nucleic acid may be, for example, DNA, RNA, PNA, LNA or a hybrid thereof.

As the method for immobilizing the collection molecules (25) on the surface of the quantum dot layer, chemical adsorption, covalent-binding, electric binding (electrostatic attraction), copolymerization or an avidin-biotin affinity system, and the like may be utilized.

For example, a functional group may be provided to immobilize the collection molecules on the surface of the quantum dot layer (160). The functional group may be, for example, a carboxyl group (—COOH), a thiol group (—SH), a hydroxyl group (—OH), a silane group (Si—H), an amine group (—NH) or an epoxy group.

FIG. 3 is a schematic sectional view showing a biosensor (200) related to a third example of the present invention.

Referring to FIG. 3, the biosensor (200) comprises a substrate (210), a gate electrode (240) provided on the substrate (210), an insulating layer (280) provided on the gate electrode (240), and a source electrode (220) and a drain electrode (230), provided on the insulating layer (280), respectively. Also, the biosensor (200) comprises a quantum dot layer (260) positioned on the insulating layer (280), provided so that the current flows between the source electrode (220) and the drain electrode (230), and provided so as to have electronic transition energy capable of resonating with vibration energy of a target biological material. Furthermore, the biosensor (200) may further comprise a collecting part (270) for collecting a target biological material, which is provided in the quantum dot layer (260).

In the third example, unlike the first example, the n-type channel layer (150) may not be provided and the quantum dot layer (260) electrically connects the source electrode (220) and the drain electrode (230).

On the other hand, FIGS. 4 and 5 are graphs showing detection results of cysteine.

After measuring the state without anything (blank) on the thin film transistor (TFT) element, the measurement was performed by depositing an HgSe sample on the thin film transistor (TFT) element by a spin coating method.

In FIG. 4, as can be seen from A3_Blank_HgSe_HDA, the threshold voltage of the blank state has a value smaller than the threshold voltage after HgSe_HDA is deposited, and thus it can be confirmed that the driving energy is changed.

Referring to Region A of FIG. 5, if a solution, in which cysteine is present in an aqueous solution phase, is again applied on the thin film transistor (TFT) element, it could be confirmed that the threshold voltage was changed from the HgSe_HDA graph to the cysteine graph.

Specifically, the thin film transistor (TFT) element is an element using colloidal quantum dots synthesized by a chemical wet method as an active layer, where the material comprises a semiconductor compound of Group II-VI, a semiconductor compound of Group III-V, a semiconductor compound of Group IV-VI, a semiconductor compound of Group IV or a combination thereof.

A specific quantum dot is a quantum dot nanoparticle characterized by one or more selected from the group consisting of AuS, AuSe, AuTe, AgS, AgSe, AgTe, AgO, CuS, CuSe, CuTe, CuO, CdS, CdSe, CdTe, ZnS, ZnSe, ZnTe, ZnO, HgS, HgSe, HgTe, AuSeS, AuSeTe, AuSTe, AgSeS, AgSeTe, AgSTe, CuSeS, CuSeTe, CuSTe, CdSeS, CdSeTe, CdSTe, ZnSeS, ZnSeTe, ZnSTe, HgSeS, HgSeTe, HgSTe, AuAgS, AuAgSe, AuAgTe, AuCuS, AuCuSe, AuCuTe, AuZnS, AuZnSe, AuZnTe, AuCdS, AuCdSe, AuCdTe, AuHgS, AuHgSe, AuHgTe, AgZnS, AgZnSe, AgZnTe, AgCuS, AgCuSe, AgCuTe, AgCdS, AgCdSe, AgCdTe, AgHgS, AgHgSe, AgHgTe, CuZnS, CuZnSe, CuZnTe, CuCdS, CuCdSe, CuCdTe, CuHgS, CuHgSe, CuHgTe, ZnCdS, ZnCdSe, ZnCdTe, ZnHgS, ZnHgSe, ZnHgTe, CdHgS, CdHgSe, CdHgTe, CdHgZnTe, CdZnSeS, CdZnSeTe, CdZnSTe, CdHgSeS, CdHgSeTe, CdHgSTe, HgZnSeS, HgZnSeTe, HgZnSTe; GaN, GaP, GaAs, GaSb, InN, InP, InAs, InSb, GaNP, GaNAs, GaNSb, GaPAs, GaPSb, InNP, InNAs, InNSb, InPAs, InPSb, GaInNP, GaIn-NAs, GaInNSb, GaInPAs, GaInPSb, SnS, SnSe, SnTe, PbS, PbSe, PbTe, SnSeS, SnSeTe, SnSTe, PbSeS, PbSeTe, PbSTe, SnPbS, SnPbSe, SnPbTe, SnPbSSe, SnPbSeTe, SnPbSTe, Si, Ge, SiC, and SiGe.

The surface of the quantum dot produced by the chemical wet method is surrounded by an organic or inorganic ligand, which can be substituted to change chemical and physical properties. In the present invention, the biological material can be selectively detected by using the property changed as the surface of the quantum dot is substituted with various ligands. By substituting the ligand of the initial HgSe active layer with HDA, it is possible to control so that a large change appears when the cysteine has removed the HDA and attached to the active layer as a ligand, and it is possible to induce so that other biological materials as well as the simple cysteine also exhibits the same effect.

As the method of applying quantum dots to a biosensor, a spin coating method is used. The quantum dots may be deposited on the surface of the sensor through interlayer deposition and utilized as an active layer to detect biological materials. If a solution, in which a biomolecule to be detected is dissolved, is applied on the sensor spin-coated with the quantum dots, a ligand substitution reaction takes place on the surface of the quantum dot, whereby as the electrical property of the active layer changes, it can be confirmed that the threshold voltage changes.

This is a phenomenon that appears as the electrical characteristics of the entire sensor are changed, which is influenced by the concentration of the material.

The electrical characteristics of the sensor can be measured using the thin film transistor (TFT) element and a semiconductor analyzer. The quantum dots may be deposited on the element designed such that as the measured voltage changes the gate voltage between −10 V and 10 V, the electrical characteristic change of the active layer may be measured, thereby measuring the changed value to this, and then they may detect the electrical characteristic change by applying a material to be detected to the surface. Furthermore, by changing the voltage value of the gate due to the characteristics of the TFT element, it is also possible to detect various different types of biological materials utilizing the characteristics of the deposited state of other materials as well as the HgSe quantum dots used in this experimental example.

This experimental example is that the threshold voltage change is measured by substituting the ligand for the n-type doped material using the characteristics of HgSe. In addition, the measured current value has an off current of $10^{-8}$ and an on current of $10^{-4}$, which is a phenomenon that appears as the biological material applied on the surface causes the change in the property of the active layer.

If the p-type active layer is utilized, it is also possible to apply the voltage value in the reverse direction of 10 to −10 V and when the voltage having a higher or lower on/off point is required, the measurement is possible while changing the voltage.

The preferred examples of the present invention as described above are disclosed for illustrative purposes, which can be modified, changed and added within thought and scope of the present invention by those skilled in the art and it will be considered that such modification, change and addition fall within the following claims.

INDUSTRIAL APPLICABILITY

According to the biosensor related to at least one example of the present invention, it can measure the current change of the quantum dot layer depending on the electronic-vibrational energy transfer between the quantum dot layer and the target biomolecules, thereby detecting the biological material.

The invention claimed is:

1. A biosensor comprising:
a substrate;
a gate electrode provided on the substrate;
a source electrode and a drain electrode, provided on the substrate;
an insulating layer provided on the substrate and separating each of the source electrode and the drain electrode from the gate electrode;
an n-type channel provided between the source electrode and the drain electrode; and
a quantum dot layer provided on the n-type channel, wherein the quantum dot layer has an electric potential that changes according to a transfer of electronic-vibrational energy between a target biological material and the quantum dot layer,
wherein the quantum dot layer comprises colloidal quantum dots.

2. The biosensor according to claim 1,
comprising a collecting part for collecting the target biological material, wherein the collecting part is included in the quantum dot layer.

3. The biosensor according to claim 2,
wherein the collecting part comprises one or more collection molecules.

4. The biosensor according to claim 3,
wherein the one or more collection molecules are immobilized on a curved surface portion of the quantum dot layer.

5. The biosensor according to claim 1,
wherein the quantum dot layer comprises one or more compounds selected from the group consisting of CdS, CdSe, CdTe, ZnS, ZnSe, ZnTe, ZnO, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, CdHgZnTe, CdZnSeS, CdZnSeTe, CdZnSTe, CdHgSeS, CdHgSeTe, CdHgSTe, HgZnSeS, HgZnSeTe, HgZnSTe; GaN, GaP, GaAs, GaSb, InN, InP, InAs, InSb, GaNP, GaNAs, GaNSb, GaPAs, GaPSb, InNP, InNAs, InNSb, InPAs, InPSb, GaInNP, GaIn-NAs, GaInNSb, GaInPAs, GaInPSb, SnS, SnSe, SnTe, PbS, PbSe, PbTe, SnSeS, SnSeTe, SnSTe, PbSeS, PbSeTe, PbSTe, SnPbS, SnPbSe, SnPbTe, SnPbSSe, SnPbSeTe, SnPbSTe, Si, Ge, SiC and SiGe.

6. The biosensor according to claim 1,
wherein the quantum dot layer comprises ligand-substituted quantum dots.

7. The biosensor according to claim 6,
wherein the ligand-substituted quantum dots are substituted with at least one of an organic ligand or an inorganic ligand.

8. The biosensor according to claim 1,
wherein the n-type channel is an n-type material selected from the group consisting of IGZO, ZnO, ZTO, IZO, IHZO, AlN, InN, GaN and InGaN.

9. The biosensor according to claim 1, wherein the gate electrode is formed of a metal.

10. The biosensor according to claim 1, wherein the biosensor is configured to measure a change in current at the quantum dot layer and detect the target biological material based on the change in current.

11. The biosensor according to claim 10, wherein the biosensor is configured to measure the change in current at the quantum dot layer when a voltage equal to or higher than a threshold voltage amount is applied between the source electrode and the gate electrode.

12. The biosensor according to claim 11, wherein biosensor is configured to measure a distance between the quantum dot layer and the target biological material based on the change in current at the quantum dot layer.

13. The biosensor according to claim 1, wherein the quantum dot layer is configured to undergo a ligand substitution reaction that causes the electric potential of the quantum dot layer to change in response to application of the target biological material to a surface of the quantum dot layer.

14. The biosensor according to claim 1, wherein the biosensor is configured to determine a concentration of the target biological material based on the change to the electric potential of the quantum dot layer.

15. The biosensor according to claim 1, wherein the biosensor is configured to measure the change in current at the quantum dot layer without destroying the target biological material during measurement.

16. A biosensor comprising:
a substrate;
a gate electrode provided on the substrate;
a source electrode and a drain electrode, provided on the substrate, respectively;
an insulating layer provided on the substrate and separating each of the source electrode and the drain electrode from the gate electrode; and
a quantum dot layer provided on the insulating layer, provided so as to electrically connect the source electrode and the drain electrode, and having an electric potential that changes according to a transfer of electronic-vibrational energy between a target biological material and the quantum dot layer,
wherein the quantum dot layer comprises colloidal quantum dots.

17. The biosensor according to claim 16,
comprising a collecting part for collecting the target biological material, wherein the collecting part is included in the quantum dot layer.

\* \* \* \* \*